US011027082B2

(12) United States Patent
Borrello

(10) Patent No.: US 11,027,082 B2
(45) Date of Patent: Jun. 8, 2021

(54) METHODS AND SYSTEMS TO ESTIMATE COMPLIANCE OF A PATIENT CIRCUIT IN THE PRESENCE OF LEAK

(71) Applicant: KONINKLIJKE PHILIPS N.V., Eindhoven (NL)

(72) Inventor: Michael Anthony Borrello, Carlsbad, CA (US)

(73) Assignee: Koninklijke Philps N.V., Eindhoven (NL)

( * ) Notice: Subject to any disclaimer, the term of this patent is extended or adjusted under 35 U.S.C. 154(b) by 258 days.

(21) Appl. No.: 15/762,883

(22) PCT Filed: Sep. 26, 2016

(86) PCT No.: PCT/EP2016/072794
§ 371 (c)(1),
(2) Date: Mar. 23, 2018

(87) PCT Pub. No.: WO2017/055195
PCT Pub. Date: Apr. 6, 2017

(65) Prior Publication Data
US 2018/0256841 A1      Sep. 13, 2018

Related U.S. Application Data

(60) Provisional application No. 62/233,483, filed on Sep. 28, 2015.

(51) Int. Cl.
*A61M 16/00*      (2006.01)
*G16H 50/20*      (2018.01)
(Continued)

(52) U.S. Cl.
CPC ...... *A61M 16/026* (2017.08); *A61M 16/0003* (2014.02); *A61M 16/024* (2017.08);
(Continued)

(58) Field of Classification Search
CPC ........ G01N 1/4077; G01N 1/40; G01N 15/14; G01N 15/1404; G01N 35/00;
(Continued)

(56) References Cited

U.S. PATENT DOCUMENTS

| 6,557,553 B1 * | 5/2003 | Borrello ............ A61M 16/0051 |
| | | 128/204.18 |
| 7,708,697 B2 | 5/2010 | Wilkinson et al. |

(Continued)

FOREIGN PATENT DOCUMENTS

| CN | 104874067 A * | 9/2015 |
| WO | 0220076 A2 | 3/2001 |
| WO | 2007047172 A2 | 4/2007 |

OTHER PUBLICATIONS

Translate CN-104874067-A (Year: 2015).*

*Primary Examiner* — Alexander A Mercado
*Assistant Examiner* — Monica S Young
(74) *Attorney, Agent, or Firm* — Daniel H. Brean

(57) ABSTRACT

A method (200) for determining compliance of a connecting circuit in a non-invasive ventilator system. The method includes the steps of: (i) providing (210) a non-invasive ventilator system, the system having a flow or pressure controller; (ii) generating (220) a test signal for the flow or pressure controller; (iii) exciting (230) the flow or pressure controller with the generated test signal for a predetermined time period; (iv) obtaining (240), during the excitation of the flow or pressure controller, one or more measurements of the non-invasive ventilator system; (v) determining (250) a vector of the obtained measurements; and (vi) processing (260) the vector to determine an estimate of a physical parameter of the circuit.

9 Claims, 3 Drawing Sheets

(51) Int. Cl.
*A61M 16/08* (2006.01)
*A61M 16/20* (2006.01)
*A61M 16/06* (2006.01)

(52) U.S. Cl.
CPC ........ *A61M 16/0875* (2013.01); *G16H 50/20* (2018.01); *A61M 16/0051* (2013.01); *A61M 16/0066* (2013.01); *A61M 16/06* (2013.01); *A61M 16/08* (2013.01); *A61M 16/0883* (2014.02); *A61M 16/205* (2014.02); *A61M 2016/0027* (2013.01); *A61M 2016/0033* (2013.01); *A61M 2016/0042* (2013.01); *A61M 2205/15* (2013.01); *A61M 2205/3344* (2013.01); *A61M 2205/70* (2013.01)

(58) Field of Classification Search
CPC ... G01N 2001/4088; G01N 2015/1418; G01N 2035/00277; G01N 2035/00475
USPC .......................................................... 73/863
See application file for complete search history.

(56) References Cited

U.S. PATENT DOCUMENTS

| | | | |
|---|---|---|---|
| 8,272,379 B2 | 9/2012 | Jafari et al. | |
| 8,418,691 B2 | 4/2013 | Jafari et al. | |
| 9,675,771 B2* | 6/2017 | Jafari | A61M 16/0051 |
| 2006/0249150 A1* | 11/2006 | Dietz | A61M 16/022 |
| | | | 128/204.18 |
| 2007/0089738 A1* | 4/2007 | Soliman | A61M 16/026 |
| | | | 128/202.22 |
| 2010/0236553 A1* | 9/2010 | Jafari | A61M 16/0875 |
| | | | 128/204.21 |
| 2011/0265795 A1* | 11/2011 | Tagawa | A61M 16/026 |
| | | | 128/205.23 |
| 2012/0037159 A1* | 2/2012 | Mulqueeny | A61M 16/06 |
| | | | 128/204.23 |
| 2012/0078542 A1* | 3/2012 | Younes | A61M 16/0051 |
| | | | 702/51 |
| 2012/0098477 A1* | 4/2012 | Gao | G01R 31/343 |
| | | | 318/798 |
| 2012/0289852 A1* | 11/2012 | Van Den Aardweg | A61B 5/085 |
| | | | 600/533 |
| 2013/0192600 A1* | 8/2013 | Eklund | A61M 16/026 |
| | | | 128/204.23 |
| 2013/0255682 A1* | 10/2013 | Jafari | A61M 16/0051 |
| | | | 128/204.21 |
| 2013/0317765 A1* | 11/2013 | Rao | A61M 16/0051 |
| | | | 702/51 |
| 2014/0034054 A1* | 2/2014 | Angelico | A61M 16/0003 |
| | | | 128/204.23 |
| 2014/0194767 A1* | 7/2014 | Zheng | G09B 23/288 |
| | | | 600/538 |
| 2014/0251329 A1* | 9/2014 | Bostick | A61M 16/122 |
| | | | 128/203.12 |
| 2014/0350429 A1* | 11/2014 | Truschel | A61M 16/0066 |
| | | | 600/533 |
| 2015/0000665 A1* | 1/2015 | Isaza | A61M 16/026 |
| | | | 128/204.23 |
| 2015/0119743 A1 | 4/2015 | Maksym et al. | |
| 2015/0335851 A1* | 11/2015 | Cullen | A61M 16/0057 |
| | | | 128/204.25 |
| 2016/0106341 A1* | 4/2016 | Adam | A61B 5/085 |
| | | | 600/538 |
| 2018/0117270 A1* | 5/2018 | Bassin | A61B 5/0826 |
| 2018/0154102 A1* | 6/2018 | Selander | A61M 16/1015 |

\* cited by examiner

METHODS AND SYSTEMS TO ESTIMATE COMPLIANCE OF A PATIENT CIRCUIT IN THE PRESENCE OF LEAK

CROSS-REFERENCE TO PRIOR APPLICATIONS

This application is the U.S. National Phase application under 35 U.S.C. § 371 of International Application No. PCT/EP2016/072794, filed on Sep. 26, 2016, which claims the benefit of U.S. Provisional Patent Application No. 62/233,483, filed on Sep. 28, 2015. These applications are hereby incorporated by reference herein.

FIELD OF THE INVENTION

The present disclosure is directed generally to methods and systems for estimating compliance of a patient-ventilator connecting circuit in the presence of leak.

BACKGROUND

The most common means of providing critical care ventilation requires intubating patients with an endotracheal tube that seals within the trachea using an inflatable cuff. Intubation offers the best means of clinically managing the airway and maintaining lung inflation, but it introduces significant risks including tissue abrasion, infection, and sedation of the patient due to extreme discomfort. Accordingly, intubation is appropriately called invasive ventilation, and the clinician's decision to intubate must be carefully considered. For a number of hospitalized patients requiring breathing support, the risks leading to adverse side effects of intubation can outweigh the benefits.

In light of significant risks of invasive ventilation, an alternative approach has been developed from home care ventilation that offers the benefit of applying support through the airway, but uses a connection such as a mask over the patient's mouth and nose, or a tracheostomy tube. This approach is called non-invasive positive pressure ventilation, or simply non-invasive ventilation ("NIV"). For non-invasive ventilation, some leak is expected and often purposely introduced in order to reduce end-tidal $CO_2$ that would otherwise be rebreathed by the patient, since a single limb circuit is most often used to connect the ventilator to the mask in a non-invasive ventilation system. In comparison, invasive ventilation typically uses a dual-limb connecting circuit that separately carries exhaled gases. This prevents rebreathing of $CO_2$ in invasive ventilation which therefore requires no leak.

For non-invasive ventilation breath modes with the goal of providing accurate volume delivery, such as the average volume assured pressure support (AVAPS) system, accurate exhaled volume measurements can be essential. However, accurate exhaled volume measures are difficult to achieve in non-invasive ventilation systems since there are volume losses in the patient connecting circuit. These losses include transient compressional losses due to connecting circuit compliance, as well as continuous losses due to intentional leak flow. In terms of either monitored or delivered volume accuracy, circuit losses become ever more significant as the volumes become smaller. And so this can ultimately limit applicability of NIV to smaller patients. If losses can be suitably identified, characterized, and compensated, then the volume measurement accuracy can be improved. And non-invasive ventilation systems can be extended to smaller patients.

The compensation of volume losses requires information about the compliance and leak in the circuit. Although intentional leak can be determined, such as through calibration during patient setup, determining circuit compliance is challenging for an NIV single limb circuit since there is a leak present. In invasive ventilation systems, compliance of the patient circuit can be measured during ventilator setup by completely blocking and pressurizing the patient circuit which does not have leaks. In contrast, the intentional leaks in a non-invasive ventilation system are engineered so that they cannot be easily blocked, thus always assuring that $CO_2$ is properly flushed during breath delivery. As a result, the non-invasive ventilator patient circuit cannot be easily pressurized over an ever increasing volume in the same manner as invasive patient circuits, where leak is usually not an issue.

Accordingly, there is a need in the art for non-invasive ventilation systems that can estimate the compliance of a patient-ventilator connecting circuit in the presence of leak, thereby improving volume measurement and delivery.

SUMMARY OF THE INVENTION

The present disclosure is directed to inventive methods and systems for calculating, measuring, and testing the compliance of a connecting circuit in the presence of leak in a non-invasive ventilator system. Various embodiments and implementations herein are directed to a non-invasive ventilator system in which random flow fluctuations are generated and utilized in the patient-ventilator circuit. The flow and pressure measures that result from the random flow fluctuations are used to estimate the circuit parameters of compliance and leak.

Generally in one aspect, a method for determining compliance of a connecting circuit in a non-invasive ventilator system is provided. The method includes the steps of: (i) providing a non-invasive ventilator system, the system having a flow or pressure controller; (ii) generating a test signal for the flow or pressure controller; (iii) exciting the flow or pressure controller with the generated test signal for a predetermined time period; (iv) obtaining, during the excitation of the flow or pressure controller, one or more measurements of the non-invasive ventilator system; (v) determining a vector of the obtained measurements; and (vi) processing the vector to determine an estimate of physical parameters of the circuit.

According to an embodiment, the test signal is filtered white noise. According to an embodiment the filter is a low frequency, high cutoff, low pass filter.

According to an embodiment, the flow or pressure controller is excited for approximately seven seconds.

According to an embodiment, the measurement is proximal pressure and blower flow.

According to an embodiment, the method includes a measurement quality check; the steps of: averaging the one or more measurements obtained during a first subset of the predetermined time period; analyzing the average to determine whether a patient port of the non-invasive ventilator system was blocked and/or if the leak was insufficient during the obtaining step; and proceeding to a next step only if the patient port was blocked and/or the leak was sufficient.

According to an embodiment, the parameter vector is determined using a Moore-Penrose pseudo inverse method.

According to an embodiment, the method further includes a quality check on the computations: the step of comparing the physical parameter measurement to a predetermined range of acceptance.

According to an embodiment, the physical parameter measurement is utilized by the non-invasive ventilator system only if the measurement is within the predetermined range of acceptance.

Generally, in one aspect, a method for detecting unknown leak in an invasive ventilator system is provided. The method includes the steps of: (i) providing an invasive ventilator system having an exhalation valve and an exhalation valve flow sensor; (ii) generating a test signal for one of a flow controller, the exhalation valve, or a pressure controller; (iii) maintaining a controlled leak using the exhalation valve; (iv) exciting the flow controller, the exhalation valve, or the pressure controller with the generated test signal for a predetermined time period; (v) obtaining, during the excitation of the pressure controller, the exhalation valve, or the flow controller, one or more measurements of the invasive ventilator system, including a measurement from the exhalation valve flow sensor; (vi) determining a vector of the obtained measurements; and (vii) processing the vector to determine an estimate of physical parameters of the circuit.

Generally, in one aspect, a non-invasive ventilator system is provided. The system includes a controller configured to generate a test signal; excite the flow source with the generated test signal for a predetermined time period; obtain one or more measurements of the system; determine a vector of the obtained one or more measurements; and extract an estimate of physical parameters of the system.

Generally, in one aspect, a method for determining compliance of a connecting circuit in a non-invasive ventilator system is provided. The method includes the steps of: (i) providing a non-invasive ventilator system, the system having a flow or pressure controller; (ii) generating a test signal for the flow or pressure controller; (iii) exciting the flow or pressure controller with the generated test signal for a predetermined time period; (vi) obtaining, during the excitation of the flow or pressure controller, one or more measurements of the non-invasive ventilator system; (v) averaging the one or more measurements obtained during a first subset of the predetermined time period; (vi) analyzing the average to determine whether a patient port of the non-invasive ventilator system was blocked and/or insufficient during the obtaining step, and proceeding to a next step only if the patient port was blocked and/or sufficient; (vii) determining a vector of the obtained measurement; (viii) extracting an estimate of a physical parameter of the system from the determined vector; and (ix) comparing the physical parameter estimate to a predetermined range of acceptance.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of a non-invasive ventilator ("NIV") system and method. More generally, Applicant has recognized and appreciated that it would be beneficial to provide a non-invasive ventilator system and method that accurately measures volume, and thus improves volume delivery, by determining the compliance of a connecting circuit in the presence of leak. For example, the patient-ventilator circuit of the non-invasive ventilator system is excited with random flow fluctuations, meaning that, for example, the random flow fluctuations are generated using electronic control signals that are supplied to a flow valve that connects with the patient-ventilator circuit to cause an activation of a pressure response within that circuit. The measurements of the exciting flow input and the pressure response that result from the random flow fluctuations are used to estimate the circuit parameters of compliance and leak.

According to an embodiment, instead of using static measurements that separately look at leak resistance and delta-pressure to delta-volume changes, the patient circuit is treated as a dynamic system with a time constant comprising the volume within as compliance, and a flow-sensitive resistance as the leak. This linear model representation with time varying parameters is known as a linear parameter varying ("LPV") model, a type of nonlinear model. By using the LPV model, the nonlinear system can be described as a linear parametric model by extending the parameter space. This allows solution of the parameters using linear least squares methods. Since flow and pressure in the patient circuit are made positive during the calibration, the parameterization doesn't need to deal with the sign of either pressure or flow. This makes the linear parametric model and calculations much simpler than if the variables were permitted to change sign.

According to an embodiment, therefore, is a method for determining compliance and leak resistance with one or more of the following elements: (i) a step-wise procedure for measuring circuit response: (ii) a method of activating the patient circuit with a generated signal; (iii) a non-linear model of the patient circuit that embodies compliance and leak characteristics, and which is used to create a linear regression vector for parameter estimation; and (iv) a parameter estimation that determines the parameters of leak resistance and circuit compliance using the non-linear model and obtained measurements.

Figure 1:
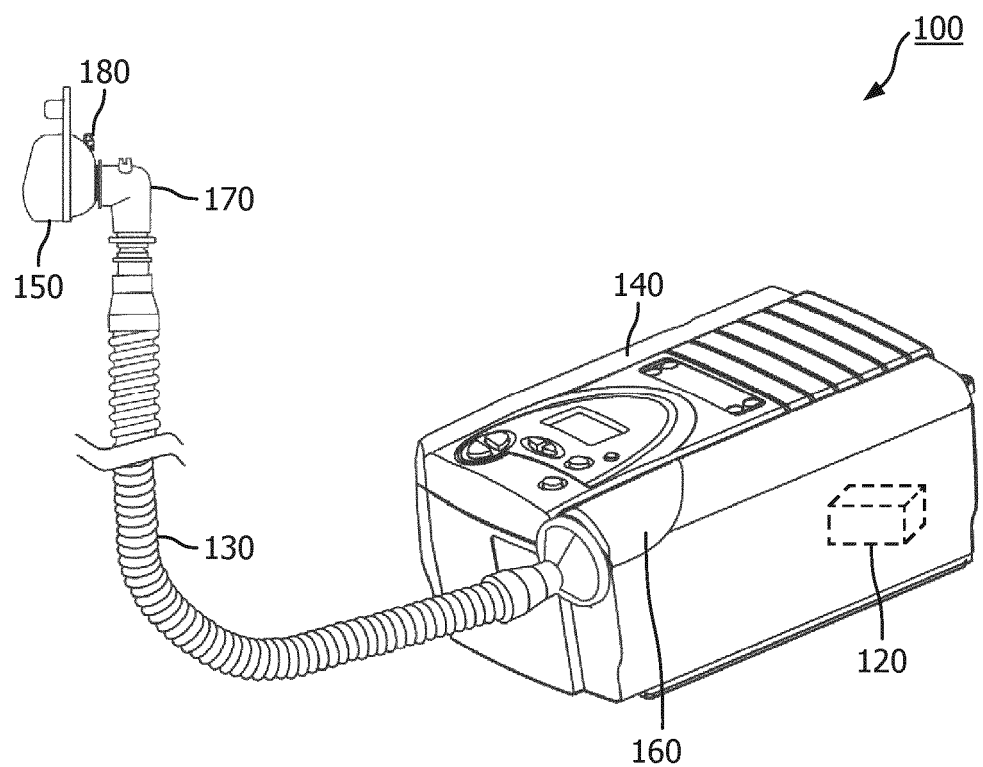
FIG. 1 is a schematic representation of a non-invasive ventilator system in accordance with an embodiment.

Referring to FIG. 1, in one embodiment, is a representation of an example non-invasive ventilation system 100. The system includes a gas source which can be any gas, including but not limited to atmospheric air and oxygen, among others. The gas source is expelled from the ventilator with a predetermined pressure. The system also includes a controller 120, which is a conventional microprocessor, an application specific integrated circuit (ASIC), a system on chip (SOC), and/or a field-programmable gate arrays (FPGA), among other types of controllers. A controller may be implemented with or without employing a processor, and also may be implemented as a combination of dedicated hardware to perform some functions and a processor (e.g., one or more programmed microprocessors and associated circuitry) to perform other functions.

The controller 120 can be coupled with or otherwise in communication with any needed memory, power supply, I/O devices, control circuitry, and/or other devices necessary for operation of the ventilator according to the embodiments described or otherwise envisioned herein. For example, in various implementations, a processor or controller may be associated with one or more storage media. In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

According to an embodiment, the controller 120 is configured or programmed to function as a blower controller to coordinate and control the blower functions of the non-invasive ventilator. For example, the blower controller can control the rate and strength of the blower(s) of the system, thereby controlling or directing the flow through the circuit. According to another embodiment, the blower controller is a separate component, preferably in communication with controller 120, although the multiple functions of the system can be otherwise coordinated. Although this embodiment uses the blower flow controller to excite the circuit, any type of flow source, including for example proportionally controlled compressed gas valves, could be utilized where the source provides a means of actual flow and pressure measurements.

The non-invasive ventilator includes a tube or tubing 130 that delivers gas from the remote ventilator component 140 to the user interface 150. User interface 150 can be, for example, a face mask that covers all or a portion of the user's mouth and/or nose. There may be masks of many different sizes to accommodate patients or individuals of different sizes, and/or the mask may be adjustable. As another alternative, user interface 150 may fit within or on, or otherwise interact with, a tracheostomy tube. Accordingly, the user interface 150 may be a variety of sizes to accommodate tracheostomies of different shapes and sizes. The user interface is configured to fit with at least a portion of the patient's airway and includes an exhalation port 180. The non-invasive ventilation system can comprise a distal gas flow sensor 160 at the end of the tubing near the remote ventilator component 140, and a proximal pressure sensor 170 at the end of the tubing near the user interface 150. Either of distal gas flow sensor 160 or proximal pressure sensor 170 may comprise, for example, two or more sensors. For example, distal gas flow sensor 160 can comprise a blower flow sensor and an $O_2$ valve sensor. Further, any of the sensors may be external or internal to the ventilator. Controller 120 is configured to receive sensor data from both distal gas flow sensor 160 and proximal pressure sensor 170, either through wired or wireless communication.

Figure 2:
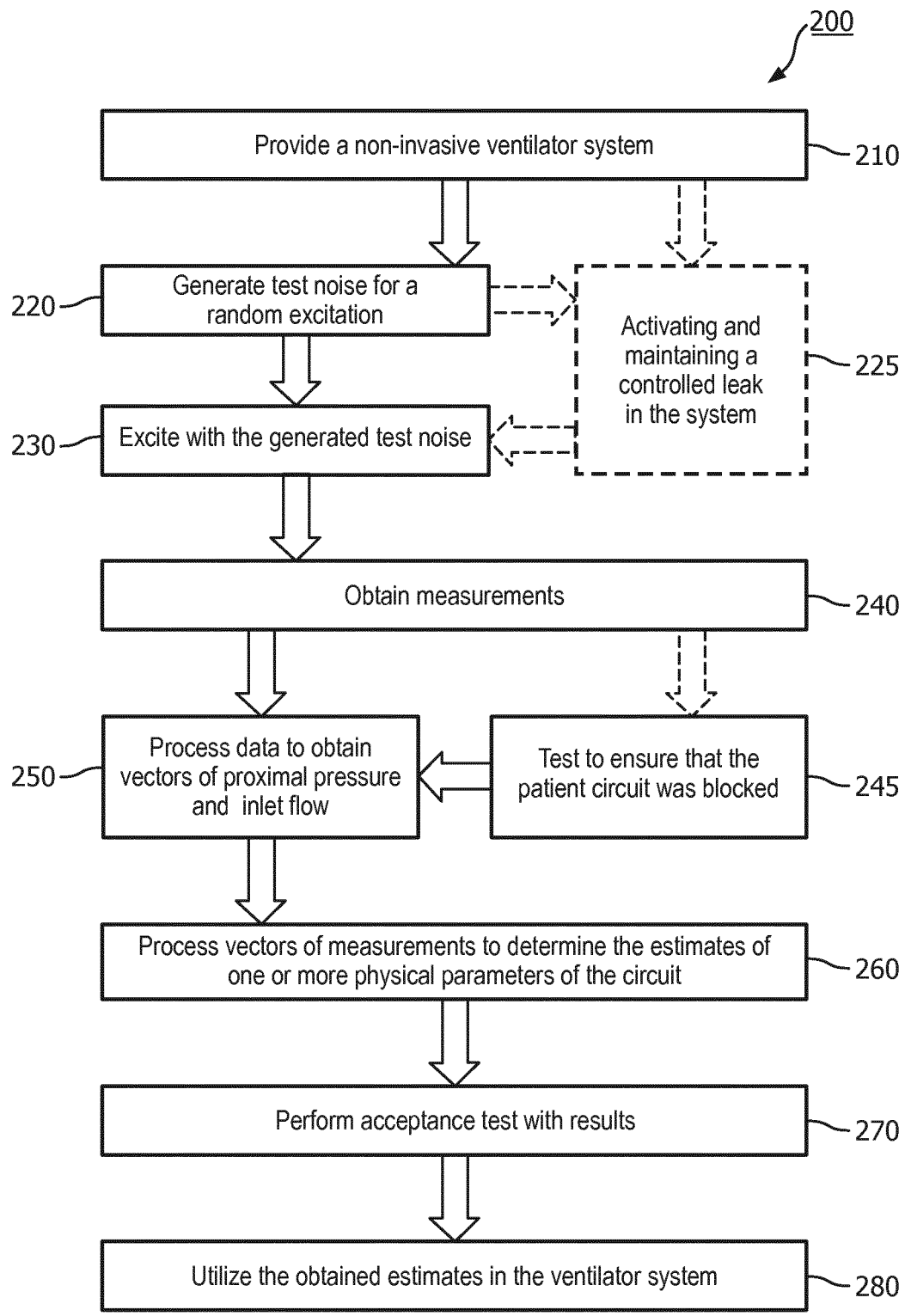
FIG. 2 is a flowchart of a method for determining the compliance of a connecting circuit in the presence of leak within a non-invasive ventilator system, in accordance with an embodiment.

Referring to FIG. 2, in one embodiment, is a flowchart of a method 200 for calculating, measuring, and testing the compliance of a connecting circuit in the presence of leak in a non-invasive ventilator system. At step 210, a non-invasive ventilator system 100 is provided. The non-invasive ventilator system can be any of the embodiments described or otherwise envisioned herein.

At step 220, the system generates a test signal. As described in greater detail below, according to an embodiment, a noise signal is synthesized or generated by filtering white noise through a filter. For example, the signal can be white noise that is subsequently filtered through a low frequency, high cutoff, low pass filter, although many other synthesis and filtering processes are possible. According to an embodiment, the system concentrates the excitation energy over the range of frequency where the system is expected to respond to excitation, namely the system's modes.

According to an embodiment, in order to prevent the signals from reaching negative values, the generated excitation noise can be offset by a bias. For example, as described in detail below, the excitation noise can be offset by a bias such as approximately 40 lpm, among others. According to an embodiment, the bias in the random flow excitation can be automatically set according to the size of the leak being determined. To accommodate a wider range of leak in the non-invasive single limb circuit, down to almost zero for example, an additional step can be added to pressurize the circuit using a pressure servo, measure the average flow during pressurization, and then use that average flow as the bias for the random flow excitation. Thus, if there is a bias target pressure in mind, the system can: (1) apply a steady pressure control to the blocked patient circuit and read the steady state bias flow; (2) use that steady state flow as the bias for the random flow noise excitation; and (3) proceed to calibration.

At step 230, the ventilator is excited with the generated test signal. Thus, the generated test signal can be a generated electronic signal that is supplied to the patient-ventilator circuit in order to cause an activation of the circuit. As described in greater detail below, according to an embodiment, at each millisecond for seven seconds the blower flow control is excited with the generated test signal, although many other time frames are possible. For example, other time frames can be engineered depending on the problem to be addressed and/or system to be utilized. According to an embodiment, the following equations are utilized: 1/duration of excitation=spectral resolution, and ½*sample time=highest frequency measured. Accordingly, the circuit is excited with flow, and flow and pressure measurements are obtained by utilizing the blower to track a flow trajectory. However, according to another embodiment, the blower can track a pressure trajectory, excite the circuit with a pressure, and read flow as the response.

For use in an invasive ventilation system, step 230 may alternatively excite the system using the exhalation valve. In this embodiment, the flow valve source may provide a constant flow of gas and the exhalation valve is modulated to interrupt the flow by commanding it with the random noise source or the test signal. The modulation of the exhalation valve creates pressure or flow fluctuations in the circuit. It may be noted that the random noise source or the test signal may be combined with another exhalation valve signal that creates a known leak rate, as explained below.

At step 240, according to an embodiment, values for $P_{prox}(m)$ (the pressure measured by the proximal pressure transducer through the proximal sense line at the patient connection), $Q_b(m)$ (the unfiltered blower flow) and/or $\hat{\omega}_{tach}(n)$ are captured for one or all of milliseconds 1 through 7000. Other values may be obtained during the excitation step.

At optional step 245, according to an embodiment, measurements or values obtained during some subset of time (such as the last four seconds, for example) are averaged to test that the patient port was blocked during the measurements, or if the leak is insufficient. If the test fails, then the process halts and the system can report that the patient port was not blocked. If the blocked patient test passes, the measurement matrix $\phi$ and the model output, $z=(z(1) \ldots z(2))$ can be filtered and populated using the $P_{prox}$ and $Q_b$ measurements. According to an embodiment, if the leak is too small the pressure will not be adequately controlled if flow is utilized. To address this issue of systems with small leak, pressure could be utilized to excite the circuit and flow could be read. For example, in invasive ventilator systems, the exhalation valve could be utilized to create an additional known leak which could also address this issue.

At step 250 the pressure and flow measurements are obtained and processed into vectors. This can be accomplished, for example, by a variety of different mechanisms, including those known in the art.

At step 260 of the method, the vectors are processed in the estimator. According to one embodiment, a parameter vector is calculated using Moore-Penrose pseudo inverse, which is one way to solve the least squares problem, although other methods are possible. The estimator output parameters are analyzed in order to determine the physical parameter estimates. For example, since the physical parameters are coupled in the estimator parameters and wrapped up in nonlinearity, they can be unwrapped from the estimator parameters, as described in greater detail below.

At step 270, according to an embodiment, the results are evaluated according to specified range or bounds of acceptance and will fail the test if the result is not within the range. For example, minimums and maximums may be set for one or more of the measurements, and the results may fail if they do not fall within the specified range. The range may be determined by a user, experimentally, or from a catalog of ranges.

At step 280, results that pass the tolerance test are utilized in the non-invasive ventilation system calculations to improve volume measurement and delivery.

According to an embodiment, compliance may not be constant for all pressures. Often, the compliance measurements are not primarily the compliance of the material that comprises the wall of the patient tubing, but is instead the volume and compressibility of the gas within the walls of the tubing. However, with some tubing materials such as re-useable silicon, the tubing can have a significant effect on the compliance in a pressure-dependent manner. Therefore, as pressure increases, the wall material may stretch. To accommodate these materials, according to an embodiment, the method can be further modified such that excitation with random flow occurs over a series of increasing bias flows. At each separate bias flow, the nominal pressure can be determined. Doing separate computations for compliance at each of these bias levels will result in a compliance value being determined as a function of average pressure.

According to an embodiment, the methods described or otherwise envisioned herein can be utilized for invasive ventilation systems as well. Although the method requires leak in the system, it can be modified to function with invasive ventilation systems where the leak can be provided by an exhalation valve. Since the invasive circuit does not have intentional leak, the presence of an exhalation valve allows the creation of a known leak, as shown in step 225 of FIG. 2. Using the method described herein, the estimate of leak from the model and the actual leak as measured by the exhalation valve flow sensor, are utilized to determine any unknown leak in the circuit.

According to such a system, there would be a dual limb patient circuit attached to the ventilator, with one end at the port providing the flow source and the other end at the exhalation valve port. Measurements provided at the flow source include the flow into the circuit and inlet pressure, measurements at the exhalation valve, flow and pressure.

According to an embodiment, the exhalation valve is utilized, together with its flow sensor, to manage a known, fixed leak (see step 225 of FIG. 2). For example, a controllable leak can be accomplished by throttling the exhalation valve in feedback with the exhalation sensor at the same time the flow valve tracks the random input signal. The control loop for the exhalation valve leak control could be configured or tuned to have a low frequency roll-off such that the exhalation valve does not try to respond to the leak or follow the random fluctuations. Instead the system maintains an average flow equal to the control loop set-point. Thus the exhalation valve appears to be a fixed leak similar to the exhalation port leak of a single limb, non-invasive circuit. According to an embodiment, an advantage of this approach would be that in contrast to a single limb circuit, there may be a flow sensor at the exhalation valve of the invasive system providing a leak flow measure. Accordingly, the leak is measured rather than estimated, and only the compliance of the system must be estimated.

The calibration procedure is performed as explained herein, where the circuit is excited with random flow or pressure noise. Flow and pressure measurements are obtained, and can be obtained from both ends of the patient circuit. The measurements can be utilized to obtain the compliance as described herein, although for invasive ventilation the system will also include a model that additionally identifies the circuit flow resistance. According to a method using an invasive ventilator, step 210 comprises providing an invasive ventilator system, the system comprising an exhalation valve and an exhalation valve flow sensor.

Exhalation Port Leak Resistance and Circuit Compliance Calibration

According to an embodiment, a dynamic model is described that combines non-linear leak with compliance to estimate both components at the same time. The method estimates the total leak that exists in the circuit, including leaks that might not have been intentionally engineered into the circuit, or any variation that might exist in the intentionally engineered leaks. The calibration can provide estimates for all possible combinations of non-invasive ventilation single limb patient circuit compliances and port leak resistances, including but not limited to combinations of active humidification accessories, water traps, and other components. According to an embodiment, therefore, it is assumed that all port leak devices fit the general quadratic 2-parameter pressure-flow model.

According to an embodiment, the calibration of the circuit compliance and port leak procedure can be performed, for example, immediately after the patient circuit flow resistance calibration. For example, this calibration time can take just 7 seconds to complete, according to one embodiment. The flow resistance calibration can be performed, for example, with a patient connection port left unblocked so that the flow mainly travels through that port. For compliance and exhalation port leak compliance, a user can intentionally block the patient port prior to beginning calibration. The port can be blocked through any means, including but not limited to a thumb, cap plug, and/or stopper, among others. By blocking the patient connection, the flow is forced to exit only through the exhalation port, thus providing greater back pressure and calibration of that port.

Figure 3:
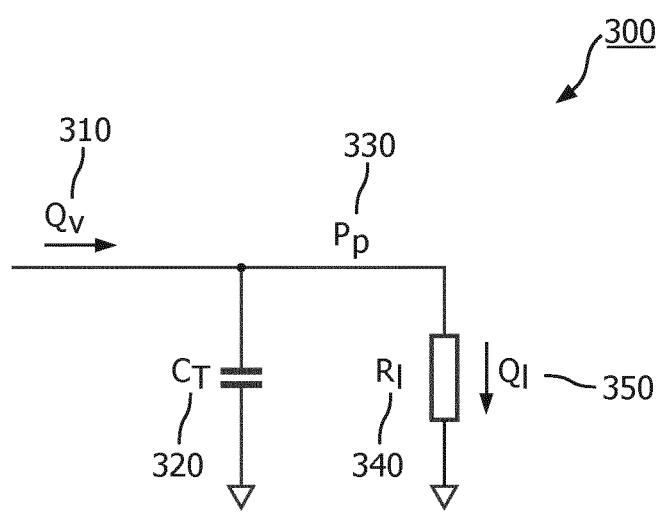
FIG. 3 is a schematic representation modeling a connecting circuit, in accordance with an embodiment.

Referring to FIG. 3, in one embodiment, is a model 300 for a non-invasive ventilation system using an electrical circuit analogy where branch currents represent flows, nodal voltages represent pressures, capacitance represents pneumatic compliance, and electrical resistance, flow restriction. FIG. 3 represents a linear parameter varying system, in which component parameters vary according to the flows or pressures they influence.

Initially, all parameters are assumed to be constant and therefore comprise a strictly linear system. In FIG. 3, for example, $Q_v$ denoted by numeral 310 is the flow entering the patient circuit at the ventilator port; $C_T$ denoted by numeral 320 is the lumped compliance of the patient circuit tubing, mostly attributed to the compression of gas within the tubing; $P_p$ or $P_{prox}$ denoted by numeral 330 is the pressure measured by the proximal pressure transducer through the proximal sense line at the patient connection; $R_l$ denoted by numeral 340 is the lumped resistance of circuit leak near the patient, mostly attributed to the fixed leak; and $Q_l$ denoted by numeral 350 is the flow through the fixed circuit leak. This model represents the circuit, attached to the ventilator, with the patient port blocked. Flow is allowed to enter the circuit at the ventilator port and only allowed to escape at the circuit leak. The proximal pressure line is connected so that $P_p$ can be measured.

Next, according to an embodiment, the pressure and flow behavior is described in terms of the parameters, with the caveat that the known non-linear structure of components are introduced as the calculations are performed. The most significant nonlinear behavior can come from the flow-pressure behavior of leak flow resistance; compliance is so nearly linear, it can be assumed that it remains constant over the expected range of operating pressure. The $P_{prox}$ pressure is determined by the net difference when inlet and outlet flow volume compresses the gas within the tubing. The variable "s" in the following equation is the Laplace operator (representing complex frequency):

$$P_p = \frac{1}{sC_T}(Q_v - Q_l) \tag{Eq. 1}$$

Lastly, the leak flow also is driven by the $P_{prox}$ pressure:

$$P_p = K_2 Q_l^2 + K_1 Q_l \tag{Eq. 2}$$

According to an embodiment, the method assumes that $P_p$, and $Q_l$ are always positive so that the method need not be concerned about the sign of flow and negative pressure, which would otherwise lead to further complications in the quadratic term. This assumption may not always be true in breath delivery, but for the calibration procedure it can certainly be constrained. With the assumed circuit model and specified excitation, $Q_v$, which will be described below, positivity is always true. This significantly simplifies the estimator.

With constant $Q_v$, $Q_l$ will match it at steady state with a steady state pressure $P_p$. However if $Q_v$ contains sufficiently rich content in a spectral sense, the system can be excited to reveal the model's dynamic parameters. To avoid using square root in formulating the linear quadratic model, $Q_l$ can be solved and the result can be substituted into Equation 1, thus eliminating $Q_l$ since it cannot be directly measured by the ventilator. Thus, the following equation remains:

$$P_p = K_2(Q_v - sC_T P_p)^2 + K_1(Q_v - sC_T P_p) \tag{Eq. 3}$$

The first term in Equation 3 can be challenging since the factors involve the differential operator (s) as well as variables. Therefore, when the last term is expanded, the result is interpreted as the square of derivatives. Expanding Equation 3 results in the following:

$$P_p = K_2 Q_v^2 - K_2 C_T 2(sP_p)Q_v + K_2 C_T^2 (sP_p)^2 + K_1 Q_v - K_1 C_T (sP_p) \tag{Eq. 4}$$

In Equation 4, $sP_p$ is written as $(sP_p)$ to emphasize the order of operations. Although the model is indeed nonlinear, factoring and grouping of measurements allow the method to treat Equation 4 as a linear parametric model which can be used to estimate the parameters by LS. But before doing so, according to an embodiment, filtering is applied by dividing each side by $(s+\gamma)$, where $\gamma$ is an (somewhat) arbitrary constant:

$$\frac{P_p}{(s+\gamma)} = \frac{K_2 Q_v^2}{(s+\gamma)} - \frac{K_2 C_T^2 (sP_p)Q_v}{(s+\gamma)} + \frac{K_2 C_T^2 (sP_p)^2}{(s+\gamma)} + \frac{K_1 Q_v}{(s+\gamma)} - \frac{K_1 C_T (sP_p)}{(s+\gamma)} \tag{Eq. 5}$$

According to an embodiment, Equation 5 can be expressed in terms of a linear parametric model:

$$z(s) = \theta^T \phi(s) \tag{Eq. 6}$$

where z is a 1×N vector of filtered proximal pressure readings evaluated as:

$$z(s) = \left(\frac{1}{s+\alpha}\right)[P_p(s)] \tag{Eq. 7}$$

and $\theta$ is the 5×1 vector of unknown parameters (to be solved):

$$\theta = \begin{pmatrix} \theta_1 \\ \theta_2 \\ \theta_3 \\ \theta_4 \\ \theta_5 \end{pmatrix} = \begin{pmatrix} K_2 \\ K_2 C_T \\ K_2 C_T^2 \\ K_1 \\ K_1 C_T \end{pmatrix} \tag{Eq. 8}$$

and $\phi(s)$ is the 5×N regression matrix of filtered measurements:

$$\phi(s) = \begin{pmatrix} \phi_1(s) \\ \phi_2(s) \\ \phi_3(s) \\ \phi_4(s) \\ \phi_5(s) \end{pmatrix} = \begin{pmatrix} \frac{Q_v^2}{(s+\gamma)} \\ -\frac{(sP_p)Q_v}{(s+\gamma)} \\ \frac{(sP_p)^2}{(s+\gamma)} \\ \frac{Q_v}{(s+\gamma)} \\ -\frac{(sP_p)}{(s+\gamma)} \end{pmatrix} \tag{Eq. 9}$$

According to an embodiment, by casting the non-linear model as a linear parametric model two things occur that should be resolved. First, the parameter space increases in size to accommodate the nonlinearity, and second, as a result the space becomes over-specified or overdetermined. Thus, when solving for $C_T$ for example there may be more ways than one to get $C_T$, and furthermore the results of $C_T$ may differ depending on where its derived. Accordingly, simulation may determine the best choice for the particular problem. Thus, Equations 7, 8, and 9 can serve as the basis for the discrete time model that is used below, and the unraveling of parameters from θ will be specified from simulation.

Target Flow for Patient Circuit Excitation

To excite the patient circuit, a noise signal can be synthesized and provided to a flow or pressure generating source that connects to the circuit to cause an activation of the circuit mode(s). According to an embodiment, a colored noise signal is synthesized by filtering white noise through a low frequency, high cutoff, low pass filter. To provide swing room and to prevent the signals from reaching negative values, the excitation noise can be offset by a 40 lpm bias.

According to one embodiment, the noise is generated using a filter input of band limited white noise, with noise power of 4.0, offset by 40 lpm. The filter parameters can be, for example: 150 tap low pass FIR Direct Form II, equiripple; density Factor: 20; sampling frequency: 1000 Hz; pass band frequency: 20 Hz; and stop band frequency: 30 Hz, −32 dB attenuation. The resulting signal is then processed. For example, once the regression matrix and vector of filtered proximal pressures is filled with data, a least squares ("LS") solution of the parameters is calculated using the Moore-Penrose pseudo inverse:

$$\theta = z\phi^T(\phi\phi^T)^{-1} \quad \text{(Eq. 10)}$$

According to an embodiment, since the physical parameters are coupled in the estimator parameters and wrapped up in nonlinearity, they can be unwrapped from the estimator parameters. Simulation and experiment with actual measurements has suggested that the best choice comes from, for example:

$$K_2 = \theta_1, \ K_1 = \theta_4, \ C_T = \frac{\theta_2}{\theta_1} \quad \text{(Eq. 11)}$$

According to an embodiment, the parametric model and the equations that use this model are first expressed as discrete time difference equations. Additionally, for non-invasive ventilation, the ventilator-supplied flow is from the blower, so $Q_b$, the unfiltered blower flow, is substituted for $Q_v$.

Processing of the model vectors for input to the final batch least squares computations can be performed on a sample-by-sample basis assuming that raw measurement samples are all acquired at an interval of T=0.001 sec and upon an increment of the index (m). Unless otherwise specified, flows are in lps and pressures are in cm $H_2O$. According to an embodiment the process is estimating parameters is run in real time as the control sequence progresses.

Example 1-2 Parameter Quadratic Leak Model Using Batch Moore-Penrose Pseudoinverse At step 1, for m=1 to 7000 the blower flow control is excited with the generated test signal. According to an embodiment the blow flow servo is initialized to 32000 rpm and the speed controller is initialized to 11000 counts. Flow is controlled using $Q_{b\_traj}(m) = Q_{NIV\_circ\_cal}(m)$ for m=1 to 7000. The non-zero initial values provide rapid acceleration of the blower, allowing the test to complete in 7 seconds, according to an embodiment. When the sequence terminates, the blower flow can be commanded back to zero. According to an embodiment, this flow controller is the controller used for non-invasive ventilation breath delivery.

According to an embodiment, as the blower control is operated using the test signal, values for $P_{prox}(m)$, $Q_b(m)$ and $\hat{\omega}_{tach}(m)$ are captured for m=1 to 7000. For this and other steps, m=1 to 7000 can be any other range, as a wide variety of ranges are possible.

At step 2, according to an embodiment, the final four seconds of data for each captured value are averaged to test if the patient port was blocked during the measurements:

$$\bar{P}_{prox} = \frac{1}{4000}\sum_{m=3000}^{7000} P_{prox}(m) \quad \text{(Eq. 12)}$$

$$\bar{Q}_b = \frac{1}{4000}\sum_{m=3000}^{7000} Q_b(m) \quad \text{(Eq. 13)}$$

$$\bar{\omega}_{tach} = \frac{1}{4000}\sum_{m=3000}^{7000} \hat{\omega}_{tach}(m) \quad \text{(Eq. 14)}$$

According to an embodiment, if $\bar{\omega}_{tach}$>45000 or 48 lpm<$\bar{Q}_b$<32 lpm or $\bar{P}_{prox}$<10 cm $H_2O$, then the test fails and all further steps in the process are aborted. The system can then report that the patient port was not blocked. However, if the blocked patient test passes, the measurement matrix and the model output, z=(z(1) . . . z(2)) can be filtered and populated using the $P_{prox}$ and $Q_b$ measurements:

$$\phi = \begin{pmatrix} \phi_1(1) & \cdots & \phi_1(7000) \\ \vdots & \ddots & \vdots \\ \phi_5(1) & \cdots & \phi_5(7000) \end{pmatrix} \quad \text{(Eq. 15)}$$

According to an embodiment, the derivative of proximal pressure measurement can be defined as:

$$P_{pDOT}(m) = \frac{P_{prox}(m) - P_{prox}(m-1)}{\Delta T} \quad \text{(Eq. 16)}$$

$$P_{prox}(0) = P_{prox}(1)$$

$$\phi_1(m) = \mathcal{F}_{LP}(Q_b^2(m)) \quad \text{(Eq. 17)}$$

$$\phi_2(m) = -2 \cdot \mathcal{F}_{LP}(P_{pDOT}(m) \cdot Q_b(m)) \quad \text{(Eq. 18)}$$

$$\phi_3(m) = \mathcal{F}_{LP}(P_{pDOT}^2(m)) \quad \text{(Eq. 19)}$$

$$\phi_4(m) = \mathcal{F}_{LP}(Q_b(m)) \quad \text{(Eq. 20)}$$

$$\phi_5(m) = \mathcal{F}_{LP}(P_{pDOT}(m)) \quad \text{(Eq. 21)}$$

$$z(m) = \mathcal{F}_{LP}(P_{prox}(m)) \quad \text{(Eq. 22)}$$

where $\mathcal{F}_{LP}(\ )$ is defined by the following low pass filter: let $y(m) = \mathcal{F}_{LP}(x(m))$, then:

$$y(m) = \left(\frac{1}{1+\gamma\Delta T}\right)[\Delta Tx(m) + y(m-1)] \text{ with } y(0) = 0 \quad \text{(Eq. 23)}$$

According to an embodiment, the filter pole is set at γ=10 rad/sec.

At step 3, the parameter vector is calculated using Moore-Penrose pseudo inverse, according to an embodiment:

$$\theta = z\phi^T(\phi\phi^T)^{-1} \quad (\text{Eq. 24})$$

According to an embodiment, this is a single step vector-matrix calculation performed after steps one and two have been completed for 7000 samples. The product $\phi\phi^T$ is a 5×5 matrix, and so its inverse is relatively simple.

At step 4, the estimator parameters are analyzed in order to determine the physical parameter estimates:

$$K_2 = \theta_1 \quad (\text{Eq. 25})$$

$$K_1 = \theta_4 \quad (\text{Eq. 26})$$

$$C_T = \frac{\theta_2}{\theta_1} \quad (\text{Eq. 27})$$

At step 5, the acceptance criteria are evaluated. According to an embodiment, the results are evaluated according to a specified tolerance and will fail the test if the result is not within the tolerance:

$$K_{2min} < K_2 < K_{2max} \quad (\text{Eq. 28})$$

$$K_{1min} < K_1 < K_{1max} \quad (\text{Eq. 29})$$

$$C_{Tmin} < C_T < C_{Tmax} \quad (\text{Eq. 30})$$

Where $K_{2min}$=30 cm $H_2O$/(l/sec)$^2$; $K_{2max}$=130 cm $H_2O$/(l/sec)$^2$; $K_{1min}$=0 cm $H_2O$/(l/sec)$^2$; $K_{1max}$=10 cm $H_2O$/(l/sec)$^2$; $C_{Tmin}$=0.5 ml/cm $H_2O$; and $C_{Tmax}$=4.0 ml/cm $H_2O$.

Example 2-1 Parameter Quadratic Leak Model Using Recursive Least Squares

According to this example, a recursive least squares (RLS) approach is utilized. According to an embodiment, at any point during this approach the circuit can be tested to determine whether the patient port was blocked during measurements, or if leak in the circuit is insufficient. If the test fails, then the process can halt and the system can report that the patient port was not blocked. If the test passes, the process can proceed to the next step. According to an embodiment, if the leak is too small the pressure will not be adequately controlled if flow is utilized. To address this issue of systems with small leak, pressure could be utilized to excite the circuit and flow could be read, according to an embodiment. For example, in invasive ventilator systems, the exhalation valve could be utilized to create an additional known leak which could also address this issue.

At step 1, for m=1 to 2000, the parameter estimate vector and covariance matrix are initialized:

$$\theta(0) = [\theta_1(0) \quad \theta_2(0)] \quad (\text{Eq. 31})$$

$$\theta_1(0) = 0.1\sqrt{\frac{\text{cm } H_2O}{\text{liter} - \text{sec}}} \quad (\text{Eq. 32})$$

$$\theta_2(0) = 0.1 \text{ cm } H_2O/\text{liter} \quad (\text{Eq. 33})$$

$$C(0) = \begin{bmatrix} 10000 & 0 \\ 0 & 10000 \end{bmatrix} \quad (\text{Eq. 34})$$

According to an embodiment, for m=1 to 2000 the following steps 2 through 7 are performed. The blower flow servo and control flow are reset using:

$$Q_{b\_traj}(m) = Q_{NIV\_circ\_cal}(m) \quad (\text{Eq. 35})$$

According to an embodiment, at step 3, the measurement vector, φ and the model output, z are updated:

$$\phi(m) = [\phi_1(m)\phi_2(m)] \quad (\text{Eq. 36})$$

$$\phi_1(m) = \mathcal{F}_{LP}[\sqrt{\max\{0, P_{prox}(m)\}}] \quad (\text{Eq. 37})$$

$$\phi_2(m) = \mathcal{F}_{LP}(Q_b(m)) \quad (\text{Eq. 38})$$

$$z(m) = \mathcal{F}_{HP}(P_{prox}(m)) \quad (\text{Eq. 39})$$

$\mathcal{F}_{LP}(\ )$ and $\mathcal{F}_{HP}(\ )$ are discrete time, low pass and high pass filters respectively. For the low pass filter, let $y(n) = \mathcal{F}_{LP}(x(n))$, and then:

$$y(n) = \left(\frac{1}{1 + \gamma\Delta T}\right)[\Delta Tx(n) + y(n-1)] \text{ with } y(0) = 0 \quad (\text{Eq. 40})$$

and for the high pass filter, let $y(n) = \mathcal{F}_{HP}(x(n))$, then:

$$y(n) = \left(\frac{1}{1 + \gamma\Delta T}\right)[x(n) - x(n-1) + y(n-1)] \quad (\text{Eq. 41})$$

with $y(0) = x(0) = 0$ and γ=3 rad/sec.

According to an embodiment, at step 4 the covariance matrix, C, is updated:

$$C(m) = \frac{1}{\lambda}\left[C(m-1) - \frac{C(m-1)\phi(m)\phi^T(m)C(m-1)}{\phi^T(m)C(m-1)\phi(m) + \lambda}\right] \quad (\text{Eq. 42})$$

where λ=0.997 can be the forgetting factor which corresponds to an ASL of 333 samples or 0.333 sec.

According to an embodiment, at step 5 the Kalman gain vector, K, is updated:

$$K(m) = \frac{C(m-1)\phi(m)}{\phi^T(m)C(m-1)\phi(m) + \lambda} \quad (\text{Eq. 43})$$

According to an embodiment, at step 6 the parameter estimate vector is updated and the estimates are extracted:

$$\theta(m) = \theta(m-1) + K(m)[z(m) - \theta^T(m-1)\phi(m)] \quad (\text{Eq. 44})$$

According to an embodiment, at step 6 the estimator parameters are analyzed to obtain the physical parameters:

$$C_T(m) = \frac{1}{\theta_2(m)} \quad (\text{Eq. 45})$$

$$R_\ell(m) = \left(\frac{\theta_2(m)}{\theta_1(m)}\right)^2 \quad (\text{Eq. 46})$$

According to an embodiment, the last 1000 values Ct and Rl are utilized for batch averaging. For example, the last second of the estimates for compliance and leak can be averaged:

$$\overline{C}_T = \frac{1}{1000} \sum_{m=1000}^{2000} C_T(m) \quad \text{(Eq. 47)}$$

$$\overline{R}_\ell = \frac{1}{1000} \sum_{m=1000}^{2000} R_\ell(m) \quad \text{(Eq. 48)}$$

According to an embodiment, the acceptance criteria are applied. The results are evaluated according to a specified tolerance and they fail if they are not within the specified tolerance:

$$R_{lmin} < \overline{R}_l < R_{lmax} \quad \text{(Eq. 49)}$$

$$C_{Tmin} < \overline{C}_T < C_{Tmax} \quad \text{(Eq. 50)}$$

Although the analysis above is examined with regard to Embodiment #1 and Embodiment #2, these are provided only as examples. Many other embodiments are described above and envisioned as variations on the non-invasive ventilation systems and methods.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for determining compliance of a connecting circuit in a non-invasive ventilator system, the method comprising the steps of:
providing a non-invasive ventilator system, the system comprising a mask configured to provide gas to a user, a flow or pressure controller and further comprising a low frequency, high cutoff, low pass filter;
generating a test signal by filtering white noise through the low frequency, high cutoff, low pass filter;
exciting the flow or pressure controller with the generated test signal for a predetermined time period, wherein excitation occurs over a series of increasing bias flows;
obtaining, during the excitation of the pressure or flow controller, a measurement of at least one of a gas pressure or flow rate of the non-invasive ventilator system;
determining a vector of pressure of the obtained measurement; and determining, using the determined pressure vector, a parameter of a pressure flow model to indicate compliance of the connecting circuit in the non-invasive ventilator system.

2. The method of claim 1, wherein the measurement is proximal pressure or blower flow.

3. The method of claim 1, further comprising the steps of:
averaging the one or more measurements obtained during a first subset of the predetermined time period;
analyzing the average to determine whether a patient port of the non-invasive ventilator system was blocked and/or if the leak was insufficient during the obtaining step; and
proceeding to said determining a vector of the obtained measurement step only if the patient port was blocked and/or the leak was sufficient.

4. The method of claim 1, wherein the generated test signal is offset by a bias.

5. The method of claim 1, wherein the vector is determined using a Moore-Penrose pseudo inverse method.

6. The method of claim 1, further comprising the step of comparing the determined physical parameter estimate measurement to a predetermined range of acceptance.

7. The method of claim 6, wherein the determined physical parameter estimate is utilized by the non-invasive ventilator system only if the determined physical parameter estimate is within the predetermined range of acceptance.

8. A non-invasive ventilator system, comprising:
a remote ventilator component configured to generate a gas source;
a user interface comprising a mask configured to provide gas to a user;
a connecting circuit configured to connect the remote ventilator component to the user interface;
at least one sensor configured to measure at least one of gas flow or pressure;
a low frequency, high cutoff, low pass pressure filter, wherein a pressure test signal is filtered; and
a controller, the controller configured to generate the pressure test signal by filtering white noise through the low frequency, high cutoff, low pass filter; excite a flow source of the remote ventilator component with the generated pressure test signal for a predetermined time period, wherein excitation occurs over a series of increasing bias flows; obtain a measurement of at least one of a gas pressure or flow rate from the at least one sensor of the system; determine a vector of pressure of the obtained measurement; and determine, using the determined pressure vector, a parameter of a pressure flow model to indicate a compliance of a connecting circuit in the non-invasive ventilator system.

9. The non-invasive ventilator system of claim 8, wherein the measurement is proximal pressure.

* * * * *